United States Patent [19]

Uhm et al.

[11] Patent Number: 5,414,161
[45] Date of Patent: May 9, 1995

[54] PROCESS FOR THE PREPARATION OF ETHANOL FROM METHANOL

[75] Inventors: Sung J. Uhm, Seoul; Sung H. Han, Kyonggi; Jun W. Oh, Seoul; Oh S. Joo, Seoul; Kwang D. Jung, Seoul; Jung Y. Beak, Seoul, all of Rep. of Korea

[73] Assignee: Korea Institute of Science and Technology, Seoul, Rep. of Korea

[21] Appl. No.: 214,240

[22] Filed: Mar. 17, 1994

Related U.S. Application Data

[60] Continuation-in-part of Ser. No. 154,709, Nov. 17, 1993, and a continuation-in-part of Ser. No. 183,344, Jan. 19, 1994, which is a continuation-in-part of Ser. No. 175,577, Dec. 30, 1993, which is a division of Ser. No. 81,107, Jun. 25, 1993, abandoned, which is a division of Ser. No. 174,263, Dec. 28, 1993.

[30] Foreign Application Priority Data

Jun. 30, 1992 [KR] Rep. of Korea ............... 92-11524
Oct. 30, 1992 [KR] Rep. of Korea ............... 92-20188
Nov. 17, 1992 [KR] Rep. of Korea ............... 93-21568
Dec. 23, 1992 [KR] Rep. of Korea ............... 92-25281
Jul. 27, 1993 [KR] Rep. of Korea ............... 93-14265

[51] Int. Cl.⁶ .................... C07C 29/147; C07C 31/18
[52] U.S. Cl. .................... 568/885; 560/232; 562/519
[58] Field of Search .................... 568/885; 560/232

[56] References Cited

U.S. PATENT DOCUMENTS 4,454,358  6/1984  Kummer et al. .................... 568/885

*Primary Examiner*—Joseph E. Evans
*Attorney, Agent, or Firm*—Oblon, Spivak, McClelland, Maier & Neustadt

[57] ABSTRACT

Ethanol is produced economically by a gas phase carbonylation of methanol with carbon monoxide followed by a hydrogenation. Specifically, the inventive process comprises:

(a) carbonylating methanol in a gas phase with carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under mild carbonylation conditions and a high GHSV(Gas Hourly Space Velocity) of methanol to produce a mixture of acetic acid and methyl acetate;

(b) separating from the production mixture in a distillation column the acetic acid as a high boiling fraction thereof, and a mixture of the methyl acetate and the co-catalyst as a low boiling fraction thereof;

(c) further separating said methyl acetate and the co-catalyst from the low boiling fraction and recycling the separated co-catalyst to the carbonylation reactor;

(d) hydrogenating the separated methyl acetate with hydrogen gas in a hydrogenation reactor in the presence of a copper-containing hydrogenation catalyst to produce ethanol at a high yield.

12 Claims, No Drawings

PROCESS FOR THE PREPARATION OF ETHANOL FROM METHANOL

REFERENCE TO RELATED APPLICATION

This application is a continuation-in-part of U.S. Ser. No. 08/154,709, which was filed on Nov. 17, 1993; and also of U.S. Ser. No. 08/183,344, filed on Jan. 19, 1994, which in turn is a continuation-in-part of U.S. Ser. No. 08/175,577, filed on Dec. 30, 1993 which in turn is a Division of U.S. Ser. No. 08/081,107, filed on Jun. 25, 1993, now abandoned, and also a Division of U.S. Ser. No. 08/174,263, filed on Dec. 28, 1993.

FIELD OF THE INVENTION

The present invention relates to a process for preparing ethanol from the methyl acetate selectively obtained by a gas phase carbonylation of methanol with carbon monoxide.

BACKGROUND OF THE INVENTION

Ethanol is an industrially important material and finds large consumptions especially in food processing and medicinal preparations and as a fuel additive. Commercialized processes for the preparation of ethanol include fermentation of sugar, various types of starch or other raw materials obtained from plants.

In parallel with the plant-based processes, extensive studies have been made to produce ethanol from coal and natural gas, now known as the most potent petroleum substitute carbon sources. As a result, several processes have been proposed. In European Patent Publication No. 0 172 431A2, assigned to the Dow Chemical Company, and U.S. Pat. No. 4,122,110, assigned to Institute Francais du Petrole, catalytic processes for producing alcohols directly from synthesis gas are disclosed. However, these processes require rather severe reaction conditions such as high pressure, and their product selectivity is undesirably low. The resulting alcoholic products from these processes are said to contain 30–60% methanol and a mixture of higher alcohols.

As another approach, U.K. Patent Publication No. 2 053 915 A, assigned to British Petroleum, describes a reaction comprising the steps of forming methanol from synthesis gas by a commercially established catalytic process and catalytically reacting or homologating the resulting methanol with synthesis gas to form ethanol. In the preferred embodiment of the catalytic reaction, selectivity to ethanol is said to be about 80% based on the amount of methanol used. However, many problems have been encountered in the commercialization of the process due to such problems as the severe reaction conditions required and the presence of considerable amounts of by-products.

As still another approach, attempts have been made to esterify acetic acid to form methyl or ethyl acetate which is then hydrogenated to form ethanol. For example, International Publication No. WO 83/034409, asigned to Davy McKee Ltd. and U.K. Patent Publication No. 2 162 172 A disclose processes for preparing ethanol, which comprise forming acetic acid by a liquid phase carbonylation of methanol, esterifying the resulting acetic acid to form methyl acetate followed by the hydrogenation thereof to form ethanol. See also B. Juran and R. V. Porcelli of Halcon SD Group, *Hydrocarbon Processing,* 85 (Oct. 1985). However, these processes for the preparation of ethanol by hydrogenating methyl acetate, including the Halcon process, have experienced serious problems including a high production cost of the methyl acetate.

As a still further approach, BASF and Humphreys & Glassgow have reported a simpler conversion process. Specifically, in European Patent Nos. 56 488 and 100 406, there is proposed a method of directly converting acetic acid into ethanol without involving an esterification step. Despite the absence of the esterification step, however, there still exist various problems: for instance, the ethanol so produced should be separated from water; and since hydrogenation is carried out at a high reaction pressure, e.g., 4000 psi, the equipment cost may also be very high.

SUMMARY OF THE INVENTION

It is, therefore, an object of the invention to provide an efficient and economical process for the production of ethanol by way of a gas phase carbonylation of methanol to selectively produce methyl acetate followed by the hydrogenation thereof.

In accordance with the present invention, there is provided a process for economically producing ethanol, which comprises:

(a) carbonylating methanol in a gas phase with carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under mild carbonylation conditions and a high GHSV(Gas Hourly Space Velocity) of methanol to produce a mixture of acetic acid and methyl acetate;

(b) separating from the mixture in a distillation column the acetic acid as a high boiling fraction thereof, and a mixture of the methyl acetate and the co-catalyst as a low boiling fraction thereof;

(c) separating the co-catalyst from the low boiling fraction and recycling it to the carbonylation reactor;

(d) introducing the separated methyl acetate from the low boiling fraction into a hydrogenation reactor; and (e) hydrogenating the methyl acetate with hydrogen gas in the hydrogenation reactor in the presence of a hydrogenation catalyst to produce ethanol at a high yield.

DETAILED DESCRIPTION OF THE PREFERRED EMBODIMENTS

In accordance with the present invention, ethanol is economically produced by conducting a gas phase carbonylation of methanol with carbon monoxide in the presence of a rhodium catalyst and a halide co-catalyst(-which is sometimes called a promoter), said carbon monoxide being optionally in admixture of hydrogen gas, under a controlled reaction condition to produce a mixture of a major amount of methyl acetate and a minor amount of acetic acid and then hydrogenating the methyl acetate with hydrogen gas to convert it to the desired end product, i.e., ethanol, at a high yield.

A. Production of Methyl Acetate

During the gas-phase carbonylation process, selectivity to the desired methyl acetate can be increased in a simple manner in accordance with the present invention. That is, the carbonylation is carried out at a shorter contact time of the reactants with the catalyst as inversely represented by a higher GHSV of methanol ranging from 1 to 100,000 $hr^{-1}$, more preferably from 500 to 50,000 $hr^{-1}$, and most preferably from 1,000 to 10,000 $hr^{-1}$; and at milder reaction conditions: i.e., a lower pressure ranging from 1 to 300 atm, more preferably from 5 to 25 atm, and most preferably from 8 to 15 atm, and a lower reaction temperature ranging from room temperature to 500° C., more preferably from 100° to 300° C. and most preferably from 150° to 270° C. to obtain methyl acetate at a higher yield.

Carbon monoxide(CO) gas is preferably pretreated by contacting the CO gas with a halogen to remove impurities, e.g., metallic carbonyl compounds, contained therein which tend to contaminate or poison the rhodium catalyst employed in the carbonylation process rather rapidly, rendering the process commercially ineffective.

Specifically, the CO gas is fed into a purification column wherein a halogen, for example, iodine, is introduced. The amount of iodine to be used is determined as a function of the flow rate of the feed gas and the column temperature. Said iodine is introduced into the column in a molar amount ranging from 0.1 to 1,000, more preferably from 0.5 to 100, and, most preferably, from 1 to 10 times the metallic content in the feed gas. Several trays may be installed in the column to ensure good mixing between the feed gas and the iodine. The column is preferably maintained at a temperature, for example, in a range from 150° C. to 200° C., to allow the metallic carbonyl impurities contained in the feed gas to react completely with the halogen gas. The metallic halides so formed, e.g., iron and/or nikel iodide, are sent to an adsorption column and adsorbed onto the adsorbent therein, producing the desired purified feed gas. Examples of the adsorbent which may be used in the purification process include active carbon, clay, alumina, silica, silica-alumina, zeolite and other adsorbents commonly used in the art. The feed gas thus purified is transferred to the carbonylation reactor wherein said methyl acetate is produced.

Further, an appropriate amount of hydrogen (e.g., about 10 mol % based on the carbon monoxide used) can be beneficially injected into the feed stream of carbon monoxide so as to further enhance the conversion rate of methanol.

After the pretreatment discussed above, the carbon monoxide may be introduced to the carbonylation reactor at a pressure near or slightly higher than the reaction pressure, e.g., 13 atm, and at a temperature preheated to a desired reaction temperature, e.g., 250° C.; and employed in a molar ratio of methanol to carbon monoxide ranging from 1:0.1 to 1:100, more preferably from 1:0.5 to 1:50, and most preferably 1:0.8 to 1:3.

Similarly, methanol is preferably preheated and vaporized to the desired reaction temperature and pressure prior to its introduction into the reaction system.

As an exemplary embodiment, carbonylation of methanol with carbon monoxide can be carried out by using $RhCl_3+CuCl_2$ as the catalyst and $CH_3I$ as the co-catalyst at the reaction temperature of 233° C. and the reaction pressure of 150 psi. Said methanol is passed through the catalyst beds at a GHSV of 5995 $hr^{-1}$ to produce 88.4 mol % of methyl acetate and 11.6 mol % of acetic acid. The production mixture together with the methyl iodide is then sent to a distillation column to separate: said acetic acid and water, if any, as the bottoms product; essentially the entire amount of the methyl iodide and an azeotropic amount of the methyl acetate as the light end product of the distillation column(wherein the azeotropic composition of $CH_3I:CH_3COOCH_3$ is 94.2 mol %:5.8 mol % at the azeotropic boiling temperature of 42.1° C.), which are recycled to the carbonylation reactor; and the remaining major portion of the methyl acetate for recovery as an intermediate fraction of the distillation column. The methyl acetate so recovered is essentially dry, which is suitable for use in producing ethanol in accordance with the present invention.

The rhodium catalyst for use in carrying out the gas phase carbonylation of methanol in accordance with the present invention comprises a rhodium compound and a second metallic component selected from the group consisting of an alkali metal, an alkaline earth metal, a transition metal and a mixture thereof; and may be prepared by depositing or impregnating a solution of the rhodium compound dissolved in water or an organic solvent, e.g., an alcohol, on an inert supporting material together with the second metallic compound and calcining the resultant at a temperature ranging from 200° to 500° C. The inert supporting material which may be used in preparing the catalyst includes active carbon, clay, alumina, silica, silica-alumina, alumina-phosphate, alumina-silica-phosphate, magnesia, zirconia and the like.

Any of the rhodium compounds, which are soluble in water or an organic solvent and can be calcined at the temperature range of 200° to 500° C., may be used. Representative of such rhodium compounds are: $RhX_3$, $RhX_3 \cdot 3H_2O$, $Rh_2(CO)_4X_2$, $[Rh(CO)X_4]Y$, $Rh_2(CO_8$, $Rh(NO_3)_3$, $[Rh(CO)_2X_2]Y$, $Rh_2O_3$, $Rh(CH_3COO)_3$, $[Rh(C_2H_4)_2X]_2$, $Rh[(C_6H_5)_3P]_2(CO)X$, Rh metal, $RhX[(C_6H_5)_3P]_2(CH_3X)_2$, $Rh(SnX_3)[(C_6H_5)P]_3$, $RhX(CO)[(C_6H_5)_3Q]_2$, $(R_4Z)[Rh(CO)_2X]_2$, $(R_4Z)_2[Rh(CO)X_4]$, $RhX[(C_6H_5)_3P]_3$, $RhX[(C_6H_5)_3P]H_2$, $[(C_6H_5)_3P]_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group. Preferably, $RhCl_3 \cdot 3H_2O$ or $Rh(N_3)$ is used.

The rhodium compound maybe employed in an amount of 0.01 to 20% by weight, more preferably 0.1 to 10%, most preferably 0.3 to 5% by weight of Rh based on the amount of the supporting material. The transition metal compound may be added in an amount of 1 to 1000 mol %, more preferably 10 to 500 mol %, most preferably 30 to 300 mol %, based on the amount of rhodium. The alkali metal or the alkaline earth metal compound may be added in an amount of 1 to 2,000 mol %, more preferably 50 to 1000 mol %, most preferably 200 to 800 mol %, based on the amount of rhodium.

The alkali metal which may be employed as the second component in the rhodium catalyst includes Li, Na, K, Rb, Cs and Fr.

The alkaline earth metal which may be employed as the second component includes Be, Mg, Ca, Sr, Ba and Ra.

The transition metal which may be employed as the second component includes Co, Ru, Pd, Pt, Os, Ir, Ni, Mn, Re, Cr, Cu, Ag, Au, Zn, Cd, Mo, W, V, Nb, Ta, Ti, Zr and Hf.

The carbonylation catalyst according to the present invention is easily prepared by adding at least one of the second metallic compounds such as $CoCl_2$, $RuCl_3$, $PdCl_2$, $PtCl_2$, $CuCl_2$, $AgNO_3$, $AuCl_3$, $CdCl_2$, $ZnCl_2$, $OsCl_3$, $IrCl_3$, $NiCl_2$, $MnCl_2$, $ReCl_5$, $CrCl_3$, $MoCl_3$, $WCl_6$, $VCl_3$, $NbCl_5$, $TaCl_5$, $TiCl_4$, $ZrCl_4$, $HfCl_4$, $LiI$, $NaI$, $KI$, $RbCl$, $BeCl_2$, $MgCl_2$, $CaCl_2$, $SrCl_2$, $BaCl_2$ and the like in a specified amount to a rhodium compound supported on the inert material.

The inventive gas phase process for selectively producing methyl acetate is carried out by using a halide co-catalyst in the presence of the rhodium catalyst.

The halide compound which may be employed as the co-catalyst includes: $CH_3I$, $CH_3Br$, $CH_3Cl$, $I_2$, $Br_2$, $Cl_2$, $HI$, $HBr$, $HCl$ and the like. Among them, $CH_3I$ is preferred.

The halide co-catalyst may be employed in a molar ratio of the co-catalyst per mole of the methanol used ranging from 0.001 to 5, more preferably from 0.01 to 1 and most preferably from 0.05 to 0.15.

B. Production of Ethanol

Ethanol is synthesized conveniently from the methyl acetate obtained in accordance with the carbonylation process of the present invention.

As described above, in the carbonylation process, methyl acetate is produced in a high selectivity, e.g., in excess of 88%, by a simple adjustment of the reaction conditions and by using a suitable catalyst, e.g., $RhCl_3 + CuCl_2$ on active carbon. From the reaction mixture, methyl acetate and the co-catalyst can easily be separated from the rest of the mixture as a low boiling fraction in a distillation column. Further, the acetic acid can be recovered from the reaction mixture as a high boiling fraction.

All or a major portion of the methyl acetate is subsequently separated from the co-catalyst in a distillation column; and the separated methyl acetate is introduced into a hydrogenation reactor to obtain ethanol while the separated co-catalyst with or without a minor portion of methyl acetate is recycled to the carbonylation reactor. In the hydrogenation reactor, the methyl acetate is hydrogenated with hydrogen freshly introduced in the presence of a hydrogenation catalyst. It is important to note that the essentially dry methyl acetate obtained from the carbonylation process of the present invention is beneficially employed in the hydrogenation process to thereby obviate the costly drying operation required in the prior art processes of producing methyl acetate from the esterification of acetic acid with methanol.

The hydrogenation catalyst which may be employed in the hydrogenation reaction includes those compounds containing copper, e.g., Cu—Co—Zn, Cu—Zn—Fe, Cu—Co—Zn—Fe, Cu—Co—Zn—Fe—Ca, Cu—Co—Zn—Mo—Na and the like, and preferably Cu—Co—Zn—Fe. The catalyst may be prepared by adding a solution of $(NH_4)_2CO_3$ dissolved in distilled water to a solution of at least one metallic compound selected from the group consisting of $Zn(OAc)_2 \cdot 2H_2O$, $Co(OAc)_3 \cdot H_2O$, $Cu(OAc)_2 \cdot H_2O$, $Fe(NO_3)_3 \cdot 9H_2O$, $(NH_4)_6Mo_7O_{24} \cdot 4H_2O$, $Ca(NO_3)_2 \cdot 4H_2O$, $NaOH$, $K_2PtCl_4$, $PdCl_2$, $RhCl_3$, $RuCl_3$, $NiCl_2$, $CrCl_3$, $WCl_3$, $OsCl_3$ and $AlCl_3$, drying the result mixture at a temperature of about 120° C. overnight and calcining the dried material at a temperature of about 450° C. and for a period of about 16 hours. The metallic compound may be employed in an amount ranging from 0.01 to 95 wt %, more preferably from 0.1 to 80 wt % and most preferably from 1 to 50 wt %.

The hydrogenation reaction may be conducted in the presence of the above-mentioned hydrogenation catalyst at a contact time of the reactants with the catalyst as inversely represented by a LHSV(Liquid Hourly Space Velocity) of methyl acetate ranging from 0.001 to 100 $hr^{-1}$, more preferably from 0.01 to 10 $hr^{-1}$, and most preferably from 0.1 to 5 $hr^{-1}$; at a temperature ranging from 50° to 400° C., more preferably from 100° to 300° C. and most preferably from 200° to 250° C.; and under a pressure ranging from atmospheric pressure to 10,000 psig, more preferably from 100 to 5,000 psig and most preferably from 500 to 1,000 psig.

The hydrogenation of methyl acetate in accordance with the present invention produces a mixture containing methanol and ethanol in a molar ratio of about 1:1. Accordingly, the reaction mixture resulting from the hydrogenation may be separated, by way of a fractional distillation, into unreacted methyl acetate, ethanol and methanol. The resulting ethanol may be subsequently reacted with the unreacted methyl acetate to produce ethyl acetate as a byproduct. The unreacted methyl acetate and said ethyl acetate, if any, are separated at the top of the distillation column and may be recycled to the hydrogenation reactor; and ethanol is recovered at the bottom of the column, while methanol is separated as an intermediate fraction and recycled to the carbonylation reactors.

As mentioned previously, in accordance with the present invention, ethanol can be economically synthesized from methyl acetate obtained in a high yield in accordance with the inventive carbonylation process.

The following Examples are given for the purpose of illustration only and are not intended to limit the scope of the invention.

EXAMPLE 1

A carbonylation catalyst was prepared as follows: $RhCl_3$ and $LiI$ were supported on active carbon by impregnating a solution of $RhCl_3$ and $LiI$ on the carbon such that 0.6% by weight of Rh based on the amount of the active carbon and 400 mol % of LiI based on the amount of Rh were supported thereon. The resulting material was then calcined at 300° C.

A reactor tube, made of titanium and having an inside diameter of 1.27 cm (0.5 inch) and a length of 40 cm, was charged with 5 g of the catalyst. The reactor tube was filled with glass fiber, pretreated in a NaOH solution, at the top and the bottom ends thereof so as to form a catalyst bed of 10 cm in length therein; and, a thermowell having an outside diameter of 0.64 cm (0.25 inch) with a thermocouple was inserted in the center of the reactor tube. The reactor tube was oil jacketed so as to heat it with a heating medium. Methanol and carbon monoxide, pretreated with iodine, in a molar ratio of 1:2.3 were introduced into the reactor tube; and were allowed to react in the presence of 10 mol % of the co-catalyst, $CH_3I$, based on the amount of the methanol used, at an inside temperature of about 233° C. under a pressure of 150 psi.

The conversion of methanol, and the yields of acetic acid and methyl acetate depending on the GHSV of methanol under the above conditions are shown in Table 1 below.

TABLE 1

| GHSV ($hr^{-1}$) | 1207 | 1568 | 1735 | 2133 | 3293 | 3652 | 4149 |
|---|---|---|---|---|---|---|---|
| Methanol conversion | 96.4 | 93.7 | 88.9 | 84.3 | 71.6 | 68.8 | 62.2 |

TABLE 1-continued

| (%) | | | | | | | |
|---|---|---|---|---|---|---|---|
| Yield of acetic acid (%) | 33.0 | 22.3 | 20.0 | 15.5 | 10.7 | 8.6 | 7.5 |
| Yield of methyl acetate (%) | 63.0 | 64.8 | 64.8 | 63.6 | 60.1 | 54.5 | 49.5 |

[1]GHSV = Gas Hourly Space Velocity($hr^{-1}$) of methanol: This is a measure of determining the amount of the reactant, i.e., gasified methanol passing through the catalyst beds per hour. The higher the GHSV, the shorter the contact time of the catalyst with the reactant becomes, rendering the amount of the reactant to be treated per hour larger.

[2]Yield of acetic acid = $\frac{\text{Mole of acetic acid produced}}{\text{Mole of methanol introduced}} \times 100$

[3]Yield of methyl acetate = $\frac{\text{Mole of Methyl acetate produced} \times 2}{\text{Mole of methanol introduced}} \times 100$

EXAMPLE 2

This Example was carried out in the same manner as described in Example 1, except that a catalyst supported on active carbon and containing 0.6% by weight of Rh based on the amount of the active carbon and 50 mol % $CuCl_2$ based on the amount of Rh, together With the different values of GHSV, was employed. The results are shown in Table 2 below.

TABLE 2

| GHSV ($hr^{-1}$) | 1979 | 3596 | 4856 | 5995 |
|---|---|---|---|---|
| Methanol conversion (%) | 98.2 | 95.8 | 87.0 | 78.7 |
| Yield of acetic acid (%) | 45.4 | 26.7 | 15.4 | 8.9 |
| Yield of methyl acetate (%) | 52.8 | 68.0 | 71.2 | 67.8 |

EXAMPLE 3

This Example was carried out as described in Example 1, except that a catalyst supported on active carbon and containing 0.6% by weight of Rh based on the amount of the active carbon and 200 mol % of NaI based on the amount of Rh was employed, and the reaction temperature and the pressure were changed to 240° C. and 200 psi, respectively, in addition to the different values of GHSV. The results are shown in Table 3 below.

TABLE 3

| GHSV ($hr^{-1}$) | 1000 | 1568 | 1735 | 2133 |
|---|---|---|---|---|
| Methanol conversion (%) | 100 | 99.9 | 100 | 99.7 |
| Yield of acetic acid (%) | 82.0 | 57.4 | 38.8 | 31.1 |
| Yield of methyl acetate (%) | 17.1 | 42.1 | 60.0 | 67.9 |

EXAMPLE 4

This Example was carried out in the same manner as described in Example 1, except that a catalyst supported on active carbon and containing 0.6% by weight of Rh based on the amount of the active carbon and 200 mol % of KI based on the amount of Rh, together with the different values of GHSV, was employed. The results are shown in Table 4 below.

TABLE 4

| GHSV ($hr^{-1}$) | 1039 | 1795 | 2997 | 4017 |
|---|---|---|---|---|
| Methanol conversion (%) | 100 | 100 | 99.7 | 96 |

TABLE 4-continued

| GHSV ($hr^{-1}$) | 1039 | 1795 | 2997 | 4017 |
|---|---|---|---|---|
| Yield of acetic acid (%) | 94.8 | 80.0 | 50.1 | 30.1 |
| Yield of methyl acetate (%) | 5.1 | 19.9 | 48.9 | 60.5 |

EXAMPLE 5

This Example was carried out as described in Example 1, except that a catalyst supported on active carbon and containing 0.6% by weight of Rh based on the active carbon and 50 mol % of $MgCl_2$ based on the Rh, together with the different values of GHSV, was employed. The results are shown in Table 5 below.

TABLE 5

| GHSV ($hr^{-1}$) | 2068 | 3417 | 4855 | 5754 |
|---|---|---|---|---|
| Methanol conversion (%) | 100 | 98.8 | 94.6 | 84.9 |
| Yield of acetic acid (%) | 89.9 | 66.6 | 43.1 | 30.0 |
| Yield of methyl acetate (%) | 8.8 | 30.6 | 49.6 | 52.3 |

EXAMPLE 6

This Example was carried out as described in Example 1, except that a catalyst supported on active carbon and containing 0.6% by weight of Rh based on the active carbon and 50 mol % of $IrCl_3$ based on the Rh was employed, and the reaction temperature was changed to 255° C., in addition to the different values of GHSV. The results are shown in Table 6 below.

TABLE 6

| GHSV ($hr^{-1}$) | 800 | 1200 | 1500 | 2000 | 2500 |
|---|---|---|---|---|---|
| Methanol conversion (%) | 99.0 | 100 | 99.7 | 99.9 | 99.8 |
| Yield of acetic acid (%) | 74.0 | 53.8 | 38.9 | 27.7 | 18.3 |
| Yield of methyl acetate (%) | 24.1 | 44.3 | 60.1 | 71.0 | 80.1 |

EXAMPLE 7

This Example was carried out as described in Example 1, except that a catalyst supported on active carbon and containing 0.6% by weight of Rh based on the active carbon and 200 mol % of $PdCl_2$ based on the Rh was employed; and the reaction temperature and the pressure were changed to 255° C. and 150 psi, respectively, in addition to the different values of GHSV. The results are shown in Table 7 below.

TABLE 7

| GHSV ($hr^{-1}$) | 1000 | 2000 | 3000 | 4000 |
|---|---|---|---|---|
| Methanol conversion (%) | 99.1 | 95.2 | 85.3 | 78.1 |
| Yield of acetic acid (%) | 54.5 | 28.5 | 16.1 | 13.2 |
| Yield of methyl acetate (%) | 43.5 | 65.5 | 67.8 | 63.7 |

EXAMPLE 8

This Example was carried out as described in Example 1, except that a catalyst supported on active carbon and containing 0.6% by weight of Rh based on the active carbon and 50 mol % of RuCl₃ based on the Rh was employed, and the reaction temperature was changed to 255° C., in addition to the different values of GHSV. The results are shown in Table 8 below.

TABLE 8

| GHSV (hr⁻¹) | 1800 | 3000 | 4200 |
|---|---|---|---|
| Methanol conversion (%) | 93 | 84 | 73 |
| Yield of acetic acid (%) | 22.3 | 10.9 | 0.8 |
| Yield of methyl acetate (%) | 68.8 | 71.4 | 61.8 |

EXAMPLE 9

This Example was carried out as described in Example 1, except that a catalyst supported on active carbon and containing 0.6% by weight of Rh based on the active carbon and 50 mol % of CoCl₂ based on the Rh was employed; and the reaction temperature was changed to 210° C., in addition to the changed values of GHSV. The results are shown in Table 9 below.

TABLE 9

| GHSV (hr⁻¹) | 1000 | 2000 | 3000 | 4000 |
|---|---|---|---|---|
| Methanol conversion (%) | 99.9 | 98.0 | 91.1 | 82.3 |
| Yield of acetic acid (%) | 45.0 | 32.3 | 19.9 | 12.3 |
| Yield of methyl acetate (%) | 53.8 | 64.6 | 70.1 | 68.9 |

EXAMPLE 10

This Example was carried out as described in Example 1, except that a catalyst supported on active carbon and containing 0.6% by weight of Rh based on the active carbon and 50 mol % of NiCl₂ based -on the Rh was employed, and the reaction temperature was changed to 210° C., in addition to the different values of GHSV. The results are shown in Table 10 below.

TABLE 10

| GHSV (hr⁻¹) | 1000 | 2000 | 3000 | 4000 |
|---|---|---|---|---|
| Methanol conversion (%) | 100 | 95.0 | 90.2 | 79.3 |
| Selectivity to acetic acid (%) | 49.9 | 39.1 | 29.1 | 18.0 |
| Selectivity to methyl acetate (%) | 50.1 | 59.9 | 70.1 | 81.3 |

EXAMPLE 11

This Example was carried out as described in Example 1, except that a catalyst supported on active carbon and containing 0.6% by weight of Rh based on the active carbon and 50 mol % of Mn based on the Rh was employed, and the reaction temperature was changed to 270° C., in addition to the different values of GHSV. The results are shown in Table 11 below.

TABLE 11

| GHSV (hr⁻¹) | 1918 | 3417 | 4722 | 5754 |
|---|---|---|---|---|
| Methanol conversion (%) | 100 | 99.8 | 95.8 | 90.7 |
| Yield of acetic acid (%) | 82.6 | 56.8 | 39.9 | 28.1 |
| Yield of methyl acetate (%) | 16.9 | 34.4 | 51.0 | 59.3 |

EXAMPLE 12

This Example was carried out as described in JExample 1, except that a catalyst supported on active carbon and containing 0.6% by weight of Rh based on the active carbon and 25 mol % of Mn and 100 mol % of Li based on the Rh was employed, and the reaction temperature was changed to 270° C., in addition to the changed values of GHSV. The results are shown in Table 12 below.

TABLE 12

| GHSV (hr⁻¹) | 2278 | 3476 | 4856 | 6235 |
|---|---|---|---|---|
| Methanol conversion (%) | 100 | 100 | 96.9 | 88.5 |
| Yield of acetic acid (%) | 87.7 | 71.7 | 53.9 | 35.8 |
| Yield of methyl acetate (%) | 4.7 | 17.7 | 31.5 | 38.1 |

EXAMPLE 13

This Example was carried out as described in Example 1, except that a catalyst supported on active carbon and containing 0.6% by weight of Rh based on the active carbon and 50 mol % of Os based on the Rh was employed, and the reaction temperature was changed to 270° C., with the different values of GHSV. The results are shown in Table 13 below.

TABLE 13

| GHSV (hr⁻¹) | 2278 | 3596 | 4856 | 6115 |
|---|---|---|---|---|
| Methanol conversion (%) | 99.1 | 97.7 | 93.0 | 85.3 |
| Yield of acetic acid (%) | 58.7 | 37.0 | 22.7 | 16.8 |
| Yield of methyl acetate (%) | 30.2 | 52.4 | 61.8 | 62.7 |

EXAMPLE 14

A hydrogenation catalyst was prepared as follows:

A mixture of 22 g of $Zn(OAC)_2.H_2O$, 25 g of $Co(OAC)_2.H_2O$, 20 g of $Cu(OAC)_2.2H_2O$ and 1.46 g of $Fe(NO_3)_3.9H_2O$ was added with 500 ml of distilled water, and the resultant solution was stirred at room temperature until the solution became clear. Thereto was slowly added a solution of 40 g of $(NH_4)_2CO_3$ dissolved in 400 ml of distilled water. Upon completion of the addition, the mixture was stirred for about 1 hr and filtered to obtain precipitates, which were washed with distilled water, dried overnight at 120° C. in a vacuum furnace, and calcined for 16 hrs at 450° C. in a furnace to produce a hydrogenation catalyst.

A fixed bed reactor was filled with 4 g of the hydrogenation catalyst prepared above and reduced with hydrogen gas at atmospheric pressure and 350° C. for 2 hrs. Thereafter methyl acetate produced in any of Examples 1 to 13 above was introduced through a preheated section into the reactor, with different values of LHSV thereof. Hydrogen was introduced into the reactor with the molar ratio of hydrogen per one mole of methyl acetate being 5 or 10. The hydrogenation was carried out at 500 psig and 260° C. The results are shown in Table 14 below.

TABLE 14

| Reaction pressure (psig) | LHSV | Molar ratio of hydrogen/ methyl acetate | Conversion of methyl acetate (%)$^{a)}$ | Yield of ethanol (%)$^{b)}$ | Yield of ethyl acetate (%)$^{c)}$ |
| --- | --- | --- | --- | --- | --- |
| 400 | 1 | 5 | 79.0 | 57.8 | 10.6 |
| 400 | 0.5 | 5 | 93.6 | 70 | 11.8 |
| 400 | 0.5 | 10 | 96.7 | 91.6 | 2.6 |
| 600 | 1 | 5 | 85.6 | 66.2 | 9.1 |
| 600 | 0.5 | 10 | 99.8 | 97.5 | 0.9 |

$^{a)}$Conversion of methyl acetate = $\frac{\text{Moles of methyl acetate reacted}}{\text{Moles of initial methyl acetate}} \times 100$ $^{b)}$Yield of ethanol = $\frac{\text{Moles of ethanol produced}}{\text{Moles of initial methyl acetate}} \times 100$ $^{c)}$Yield of ethyl acetate = $\frac{\text{Moles of ethyl acetate produced}}{\text{Moles of initial methyl acetate}} \times 100$

EXAMPLE 15

This Example was carried out as described in Example 14, except that each of the catalysts listed in Table 15 was employed in an amount of 2.5 g, methyl acetate was introduced at a LHSV of 4.4, hydrogen gas was introduced into the reactor in 1:10 molar ratio of methyl acetate to hydrogen and the reaction temperature was changed to 250° C. The results are shown in Table 15 below.

TABLE 15

| Catalyst | Conversion of methyl acetate (%) | Yield of ethanol (%) | Yield of ethyl acetate (%) |
| --- | --- | --- | --- |
| Cu-Co-Zn | 85.3 | 71.2 | 6.6 |
| Cu-Zn-Fe | 90.7 | 78.2 | 4.1 |
| Cu-Co-Zn-Fe-Ca | 92.1 | 81.3 | 4.1 |
| Cu-Co-Zn-Mo-Na | 80.5 | 61.2 | 8.8 |

EXAMPLE 16

This Example was carried out as described in Example 14, except that each of the catalysts listed in Table 16 was employed in an amount of 2 g, methyl acetate was introduced at a LHSV of 1, hydrogen gas was introduced into the reactor in a molar ratio of methyl acetate to hydrogen of 1:5 and the reaction temperature and pressure were changed to 220° C. and 400 psi, respectively. The results are shown in Table 16 below.

TABLE 16

| Catalyst | Conversion of methyl acetate (%) | Yield of ethanol (%) | Yield of ethyl acetate (%) |
| --- | --- | --- | --- |
| Cu-Co-Zn-Fe | 62.8 | 48.2 | 6.9 |
| Cu-Co-Zn-Fe-Pd | 58.2 | 44.7 | 5.7 |
| Cu-Co-Zn | 60.5 | 46.8 | 6.7 |
| Cu-Cr (Harshaw 1184T) | 23.2 | 12.6 | 5.2 |

EXAMPLE 17

This Example was carried out as described in Example 14, except that Harshaw 1106P and Girdler 66B were employed in an amount of 2 g, methyl acetate was introduced at a LHSV of 1, hydrogen gas was introduced into the reactor in a molar ratio of methyl acetate to hydrogen of 1:10 and the reaction temperature and pressure were changed to 220° C. and 600 psi, respectively. The results are shown in Table 17 below.

TABLE 17

| Catalyst | Conversion of methyl acetate (%) | Yield of ethanol (%) | Yield of ethyl acetate (%) |
| --- | --- | --- | --- |
| Cu-Zn-Al (Girdler 66B) | 78.9 | 66.8 | 5.1 |
| Cu-Cr (Harshaw 1106P) | 4.65 | 2.6 | 1.6 |

As can be seen from the above, in accordance with the present invention, ethanol can be produced economically by hydrogenating the methyl acetate obtained from the selective gas-phase carbonylation of methanol.

While the invention has been described in connection with the above specific embodiments, it should be recognized that various modifications and changes may be made by those skilled in the art to the invention which also fall within the scope of the invention as defined by the appended claims.

What is claimed is:

1. A process for producing ethanol, which comprises:
   (a) carbonylating methanol in a gas phase with carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under mild carbonylation conditions and a high GHSV(Gas Hourly Space Velocity) of methanol to produce a mixture of acetic acid and methyl acetate;
   (b) separating from the mixture in a distillation column said acetic acid as a high boiling fraction thereof, and a mixture of said methyl acetate and the co-catalyst as a low boiling fraction thereof;
   (c) further separating all or a major portion of said methyl acetate from the co-catalyst in the low boiling fraction and recycling the separated co-catalyst with or without a minor portion of said methyl acetate to the carbonylation reactor; and
   (d) hydrogenating said separated methyl acetate with hydrogen gas in a hydrogenation reactor in the presence of a copper-containing hydrogenation catalyst to produce ethanol at a high yield.

2. The process of claim 1, wherein said carbon monoxide employed in said step(a) is passed through an adsorption column provided with an adsorbent prior to its introduction into the carbonylation reactor.

3. The process of claim 2, wherein said carbon monoxide is treated with a halogen prior to its passing through the adsorption column.

4. The process of claim 1, wherein said rhodium compound employed in said step(a) is selected from the group consisting of $RhX_3$, $RhX_3 \cdot 3H_2O$, $Rh_2(CO)_4X_2$, $[Rh(CO)X_4]Y$, $Rh_2(CO)_8$, $Rh(NO_3$, $[Rh(CO)_2X_2]Y$, $Rh_2O_3$, $Rh(CH_3COO)_3$, $[Rh(C_2H_4)_2X]_2$, $Rh[(C_6H_5)_3P]_2(CO)X$, Rh metal, $RhX[(C_6H_5)_3P]_2(CH_3X)_2$, $Rh(SnX_3)[(C_6H_5)P]_3$, $RhX(CO)[(C_6H_5)_3Q]_2$, $(R_4Z)[Rh(CO)_2X]_2$, $(R_4Z)_2Rh(CO)X_4]$, $RhX[(C_6H_5)_3P_9]_3$, $RhX[(C_6H_5)_3P]H_2$, $[(C_6H_5)_3P]_3Rh(CO)H$ and $Y_4Rh_2X_2(SnX_3)_4$ wherein X is $C_1$, Br or I; Y is Na, Li or K; Z is N, As or P; Q is As, P or Sb; and R is a $C_1$ to $C_{12}$ alkyl or aryl group.

5. The process of claim 1, wherein said alkali metal is selected from the group consisting of Li, Na, K, Rb, Cs and Fr.

6. The process of claim 1, wherein said alkaline earth metal is selected from the group consisting of Be, Mg, Ca, Sr, Ba and Ra.

7. The process of claim 1, wherein said transition metal is selected from the group consisting of Cu, Ag, Au, Zn, Cd, Co, Ru, Pd, Pt, Os, Ir, Ni, Mn, Re, Cr, Mo, W, V, Nb, Ta, Ti, Zr and Hf.

8. The process of claim 1, wherein said co-catalyst is selected from the group consisting of $CH_3I$, $CH_3Br$, $CH_3Cl$, $I_2$, $Br_2$, $Cl_2$, HI, HBr and HCl.

9. The process of claim 8, wherein said co-catalyst is $CH_3I$.

10. The process of claim 1, wherein said copper containing hydrogenation catalyst employed in step(d) is selected from the group consisting of Cu—Co—Zn, Cu—Zn—Fe, Cu—Co—Zn—Fe, Cu—Co—Zn—Fe—Ca and Cu—Co—Zn—Mo—Na.

11. The process of claim 1, wherein said carbonylation in step(a) is carried out at a temperature ranging from 150° to 270° C., at a pressure ranging from 8 to 15 atm, and at a GHSV of methanol ranging from 1,000 to 10,000 $hr^{-1}$.

12. The process of claim 1, wherein said hydrogenation in step(d) is carried out at a temperature ranging from 200 to 250° C., at a pressure ranging from 500 to 1,000 psig, and at a LHSV of methyl acetate ranging from 0.1 to 5 $hr^{-1}$.

* * * * *